United States Patent
Austin et al.

(10) Patent No.: US 9,416,492 B1
(45) Date of Patent: Aug. 16, 2016

(54) SYSTEM AND METHOD FOR ADJUSTING MEASUREMENT POSITION OF SCANNING HEAD

(71) Applicant: Honeywell ASCa Inc., Mississauga (CA)

(72) Inventors: Jeffrey D. Austin, Maple Ridge (CA); Bradley Humble, Vancouver (CA); Michael J. Wardas, North Vancouver (CA); Ronald E. Beselt, Burnaby (CA)

(73) Assignee: Honeywell Limited, Mississauga (CA)

( * ) Notice: Subject to any disclaimer, the term of this patent is extended or adjusted under 35 U.S.C. 154(b) by 0 days.

(21) Appl. No.: 14/607,298

(22) Filed: Jan. 28, 2015

(51) Int. Cl.
*D21F 11/00* (2006.01)
*D21F 7/06* (2006.01)
*D21F 7/00* (2006.01)

(52) U.S. Cl.
CPC ........................................ *D21F 7/00* (2013.01)

(58) Field of Classification Search
CPC ............ D21F 11/00; D21F 7/06; G01D 11/30
USPC .................................................. 162/198, 263
See application file for complete search history.

(56) References Cited

U.S. PATENT DOCUMENTS

| 6,222,565 | B1 | 4/2001 | van Os | |
|---|---|---|---|---|
| 8,564,851 | B2* | 10/2013 | Beselt | H04N 1/053 104/95 |
| 2007/0058212 | A1* | 3/2007 | Beselt | H04N 1/04 358/474 |
| 2009/0184463 | A1* | 7/2009 | Shakespeare | B65H 20/02 271/265.01 |
| 2010/0200570 | A1* | 8/2010 | Chirico | H05B 6/145 219/619 |
| 2011/0284178 | A1* | 11/2011 | Shakespeare | D21G 9/0027 162/198 |
| 2013/0055912 | A1* | 3/2013 | Beselt | G01N 21/8901 101/147 |
| 2014/0318928 | A1* | 10/2014 | Beselt | H01B 17/34 198/617 |
| 2014/0345397 | A1 | 11/2014 | Beselt et al. | |

OTHER PUBLICATIONS

International Search Report dated Apr. 14, 2016 in connection with International Patent Application No. PCT/CA2016/000025, 3 pages.
Written Opinion of the International Searching Authority dated Apr. 14, 2016 in connection with International Patent Application No. PCT/CA2016/000025, 4 pages.

* cited by examiner

*Primary Examiner* — Mark Halpern

(57) ABSTRACT

A method includes receiving distance measurements from at least one scanning head that moves back and forth across at least one surface of a web of material on a frame. The distance measurements identify measured distances to the web. The method also includes controlling one or more actuators in order to move at least a portion of the frame to alter a position of the at least one scanning head relative to the web. The one or more actuators could be controlled so that the at least one scanning head maintains a substantially fixed offset from the web as the at least one scanning head moves back and forth. The one or more actuators could also be controlled so that the web maintains a substantially fixed position between multiple scanning heads as the scanning heads move back and forth.

20 Claims, 4 Drawing Sheets

SYSTEM AND METHOD FOR ADJUSTING MEASUREMENT POSITION OF SCANNING HEAD

TECHNICAL FIELD

This disclosure relates generally to scanning systems. More specifically, this disclosure relates to a system and method for adjusting the measurement position of a scanning head.

BACKGROUND

Sheets or other webs of material are used in a variety of industries and in a variety of ways. These materials can include paper, multi-layer paperboard, and other products manufactured or processed in long webs. As a particular example, long sheets of paper can be manufactured and collected in reels.

It is often necessary or desirable to measure one or more properties of a web of material as the web is being manufactured or processed. Adjustments can then be made to the manufacturing or processing system to ensure that the properties stay within desired ranges. Measurements are often taken using scanning heads containing sensors that move back and forth across the width of the web.

SUMMARY

This disclosure provides a system and method for adjusting the measurement position of a scanning head.

In a first embodiment, a system includes a frame configured to support at least one scanning head as the at least one scanning head moves back and forth across at least one surface of a web of material. The system also includes an actuator system configured to move at least a portion of the frame to alter a position of the at least one scanning head relative to the web.

In a second embodiment, an apparatus includes at least one interface configured to receive distance measurements from at least one scanning head that moves back and forth across at least one surface of a web of material on a frame. The distance measurements identify measured distances to the web of material. The apparatus also includes at least one processing device configured to control one or more actuators in order to move at least a portion of the frame to alter a position of the at least one scanning head relative to the web.

In a third embodiment, a method includes receiving distance measurements from at least one scanning head that moves back and forth across at least one surface of a web of material on a frame. The distance measurements identify measured distances to the web of material. The method also includes controlling one or more actuators in order to move at least a portion of the frame to alter a position of the at least one scanning head relative to the web.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
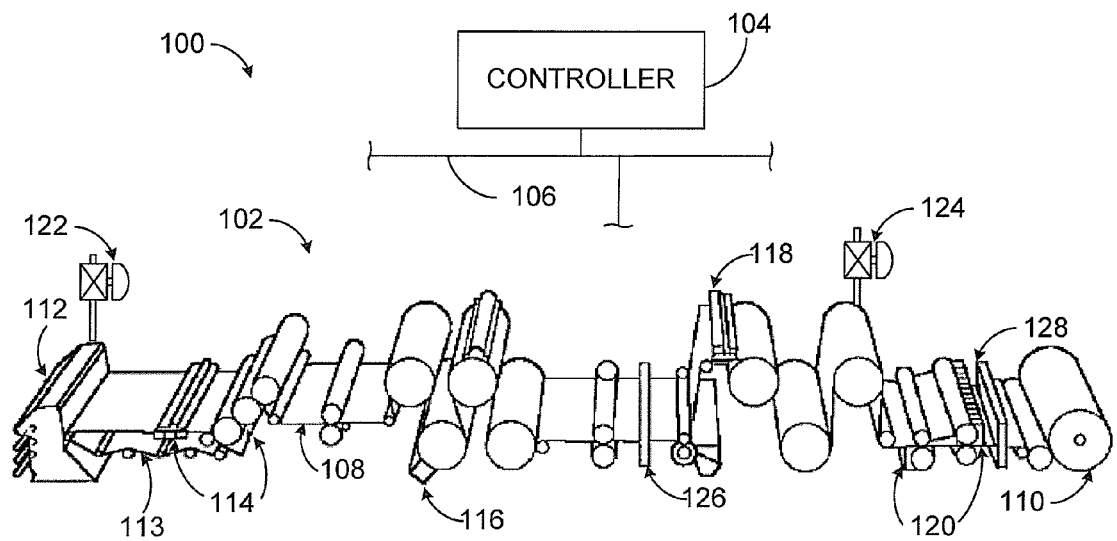
FIG. 1 illustrates an example web manufacturing or processing system according to this disclosure.

FIG. 1 illustrates an example web manufacturing or processing system 100 according to this disclosure. In this example, the system 100 includes a paper machine 102, a controller 104, and a network 106. The paper machine 102 includes various components used to produce a paper product, namely a paper web 108 that is collected at a reel 110. The controller 104 monitors and controls the operation of the paper machine 102, which may help to maintain or increase the quality of the paper web 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the web. The dilution water may be used to help ensure that the resulting paper web 108 has a more uniform basis weight across the web 108.

Arrays of drainage elements 114, such as vacuum boxes, remove as much water as possible to initiate the formation of the web 108. An array of steam actuators 116 produces hot steam that penetrates the paper web 108 and releases the latent heat of the steam into the paper web 108, thereby increasing the temperature of the paper web 108 in sections across the web. The increase in temperature may allow for easier removal of remaining water from the paper web 108. An array of rewet shower actuators 118 adds small droplets of water (which may be air atomized) onto the surface of the paper web 108. The array of rewet shower actuators 118 may be used to control the moisture profile of the paper web 108, reduce or prevent over-drying of the paper web 108, or correct any dry streaks in the paper web 108.

The paper web 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper web 108. The arrays of induction heating actuators 120 may therefore be used to control the caliper (thickness) profile of the paper web 108. The nips of a calender may also be equipped with other actuator arrays, such as arrays of air showers or steam showers, which may be used to control the gloss profile or smoothness profile of the paper web.

Two additional actuators 122-124 are shown in FIG. 1. A thick stock flow actuator 122 controls the consistency of incoming stock received at the headbox 112. A steam flow actuator 124 controls the amount of heat transferred to the paper web 108 from drying cylinders. The actuators 122-124 could, for example, represent valves controlling the flow of stock and steam, respectively. These actuators 122-124 may be used for controlling the dry weight and moisture of the paper web 108.

Additional components could be used to further process the paper web 108, such as a supercalender (for improving the paper web's thickness, smoothness, and gloss) or one or more coating stations (each applying a layer of coatant to a surface of the paper to improve the smoothness and printability of the paper web). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, systems for adjusting the measurement position of a scanning head are not limited to use with systems for producing paper products and could be used with systems that process a paper product or with systems that produce or process other items or materials (such as multi-layer paperboard, cardboard, plastic, textiles, metal webs, or other or additional materials that are manufactured or processed as moving webs).

In order to control the paper-making process, one or more properties of the paper web 108 may be continuously or repeatedly measured. The web properties can be measured at one or various stages in the manufacturing process. This information may then be used to adjust the paper machine 102, such as by adjusting various actuators within the paper machine 102. This may help to compensate for any variations of the web properties from desired targets, which may help to ensure the quality of the web 108.

As shown in FIG. 1, the paper machine 102 includes one or more scanners 126-128, each of which may include one or more sensors configured to measure one or more characteristics of the paper web 108. For example, each scanner 126-128 could include one or more sensors for measuring the caliper, anisotropy, basis weight, color, gloss, sheen, haze, surface features (such as roughness, topography, or orientation distributions of surface features), or any other or additional characteristic(s) of the paper web 108. Each scanner 126-128 includes any suitable structure or structures for measuring or detecting one or more characteristics of the paper web 108. For example, each scanner 126-128 could include one or more sensors mounted on one or more scanning heads that move back and forth across the web 108. Note, however, that stationary sensors could also be used at one or more locations of the paper machine 102.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

In order to capture accurate measurements of a web's property or properties, one or more scanning heads often need to have a specified spatial relationship with the web. For example, a single scanning head may need to maintain a substantially fixed offset distance from a web as the scanning head moves, or a web may need to remain substantially centered between multiple scanning heads as the scanning heads move. However, maintaining such specified spatial relationships can be quite difficult due to various factors. As described below, an actuator system is provided that physically moves a support on which one or more scanning heads move back and forth across a web. In this way, the actuator system allows one or more scanning heads to substantially maintain a desired spatial relationship with a web. Among other things, this can help to reduce or minimize errors in the measurements of one or more characteristics of the web.

Although FIG. 1 illustrates one example of a web manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, while FIG. 1 illustrates one operational environment in which a scanner having movable supports can be used, a scanner having movable supports could be used in any other type of system.

Figure 2A:
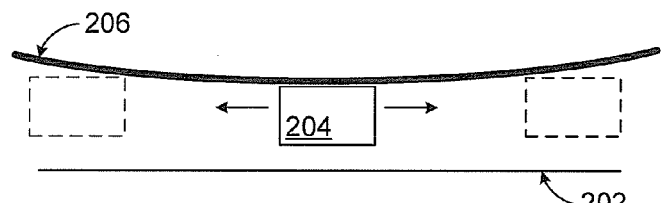
FIGS. 2A through 2C illustrate example issues that occur when using a scanning head to measure one or more characteristics of a web of material according to this disclosure.
Figure 2B:
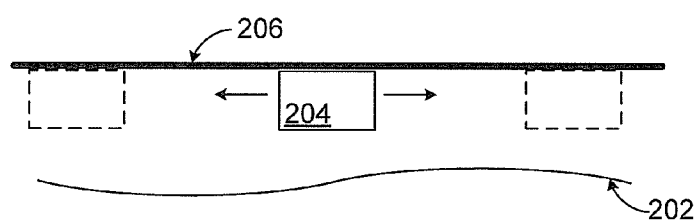
Figure 2C:
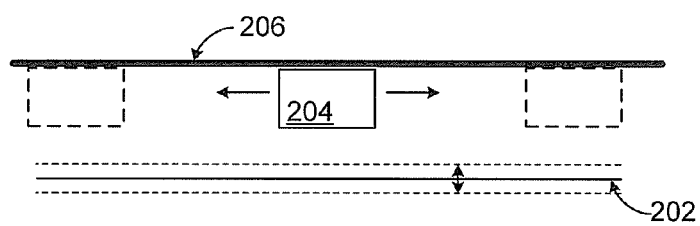

FIGS. 2A through 2C illustrate example issues that occur when using a scanning head to measure one or more characteristics of a web of material according to this disclosure. In particular, each of these figures illustrates a different mechanism that can prevent at least one scanning head from maintaining a specified spatial relationship with a web of material.

As shown in FIG. 2A, one or more properties of a web 202 of material are measured using a scanning head 204. The scanning head 204 includes one or more sensors and moves back and forth across a surface of the web 202. In this example, the scanning head 204 moves back and forth along a support 206, which holds the scanning head 204 above the web 202. However, the support 206 does not maintain a uniform distance from the web 202 and instead sags. This may be caused, for example, by manufacturing limitations that prevent the support 206 from having a sufficiently horizontal scan. This may also be caused if the support 206 is formed by rails that are anchored at opposite ends and placed under tension, where gravity or the weight of the scanning head 204 causes the support 206 to sag. Whatever the cause, the support 206 cannot maintain the scanning head 204 at a constant distance from the web 202 as the scanning head 204 moves, so the spatial relationship between the scanning head 204 and the web 202 changes (even if the web 202 is maintained in a constant position).

As shown in FIG. 2B, the support 206 here is substantially horizontal. However, the web 202 itself is non-planar, sagging down in some areas and billowing upward in other areas. This could occur for any number of reasons. For example, the web 202 can sag under its own weight due to gravity or due to higher air pressure above or lower air pressure below the web 202. Similarly, the web 202 could billow upward due to higher air pressure below or lower air pressure above the web 202. Once again, whatever the cause, the support 206 cannot maintain the scanning head 204 at a constant distance from the web 202 as the scanning head 204 moves, so the spatial relationship between the scanning head 204 and the web 202 changes.

As shown in FIG. 2C, the support 206 here is substantially horizontal, as is the web 202. However, the web 202 can flutter or dynamically change position up or down by some amount, which could occur for any number of reasons. Yet again, the support 206 cannot maintain the scanning head 204 at a constant distance from the web 202 as the scanning head 204 moves, so the spatial relationship between the scanning head 204 and the web 202 changes Note that a combination of these problems could also occur. For example, the support 206 could be non-horizontal along part or all of its length, and the web 202 could be non-planar (due to sagging, billowing, fluttering, or other causes). Also, the planarity or position of the web 202 often repeatedly changes over time, and the shape of the support 206 could also change over time.

Because of these or other problems, it is rare that a scanning head's scan path as provided by a support exactly matches the surface of a web being measured. As described in more detail below, this disclosure provides a mechanism to adjust the measurement position of at least one scanning head relative to a web. This can be used to help maintain the at least one scanning head in a desired spatial relationship with the web, even as the at least one scanning head moves back and forth across the web. By adjusting the measurement position of one or more scanning heads as the scanning heads move across the web, this approach can help to maintain a substantially constant offset between a scanning head and the web, maintain the web substantially centered between multiple scanning heads, or otherwise maintain the scanning head(s) in a desired position relative to the web.

Although FIGS. 2A through 2C illustrate examples of issues that occur when using a scanning head to measure one or more characteristics of a web of material, various changes may be made to FIGS. 2A through 2C. For example, any other or additional problems may occur that prevent a web from remaining in a desired position relative to one or more scanning heads. Also, while not shown, the support 206 could be positioned below the web 202, or multiple scanning heads could move along multiple supports on opposing sides of the web 202.

Figure 3A:
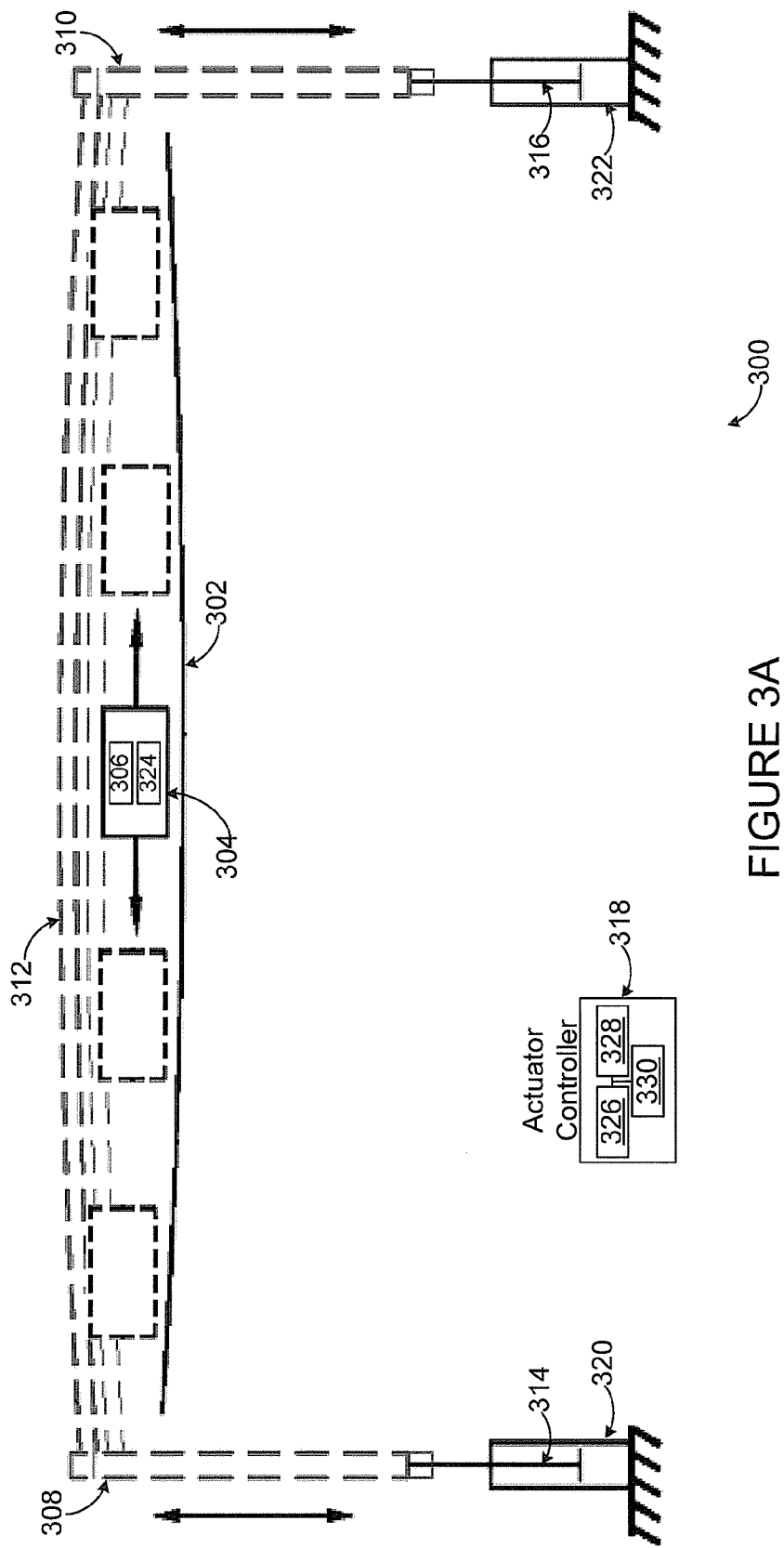
FIGS. 3A and 3B illustrate example systems for adjusting a measurement position of a scanning head according to this disclosure.
Figure 3B:
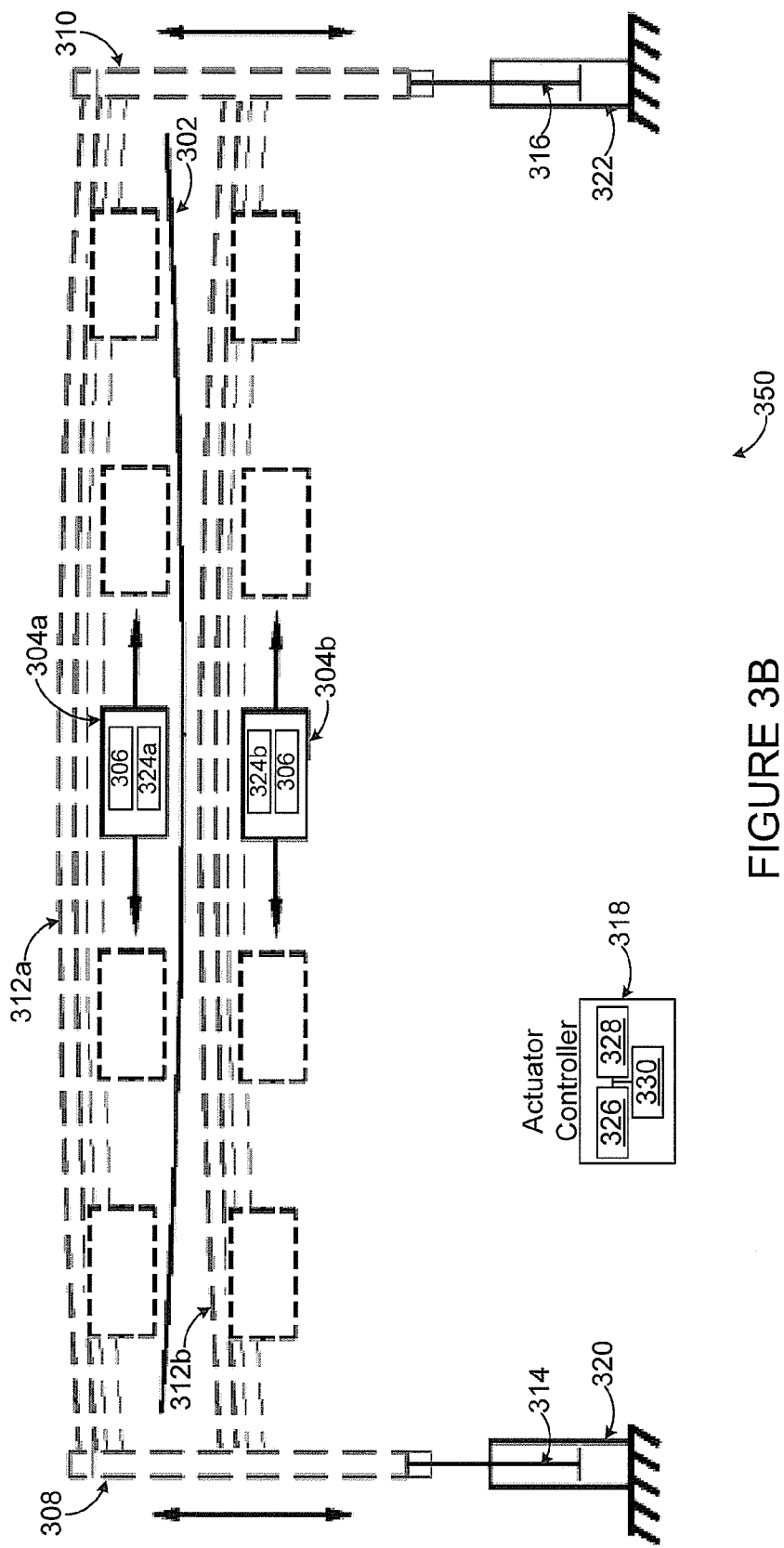

FIGS. 3A and 3B illustrate example systems for adjusting a measurement position of a scanning head according to this disclosure. In a system 300 shown in FIG. 3A, one or more properties of a web 302 of material are measured using a scanning head 304. The scanning head 304 includes one or more sensors 306 configured to measure at least one characteristic of a web of material. For example, each scanning head 304 could include one or more sensors 306 for measuring the moisture, caliper, anisotropy, basis weight, color, gloss, sheen, haze, surface features (such as roughness, topography, or orientation distributions of surface features), or any other or additional characteristic(s) of the web 302.

A frame includes two vertical supports 308-310 and a connecting support 312, which collectively form a support structure that allows the scanning head 304 to travel back and forth across the surface of the web 302. In this example, the vertical supports 308-310 are generally straight and the connecting support 312 bends upward, although each support 308-312 could have any other suitable shape. For instance, the connecting support 312 could be substantially horizontal, bend downward, or have other any other regular or irregular path. Each support 308-312 could also be formed from any suitable material(s) and in any suitable manner. Note that while the supports 308-312 are described separately here, two or more of the supports 308-312 could form an integral structure within the overall frame.

An actuator system includes two actuators 314-316 and an actuator controller 318. The actuator 314 is connected to the vertical support 308 and is located within a base 320, and the actuator 316 is connected to the vertical support 310 and is located within a base 322. Each actuator 314-316 is configured to raise and lower the associated vertical support 308-310 in order to change the position of the scanning head 304 relative to the web 302.

Each actuator 314-316 represents any suitable structure for moving a support structure to thereby move at least one scanning head, such as a linear actuator. Each base 320-322 represents any suitable structure that can receive an actuator and at least a portion of a vertical support. Note that the positioning of the actuators 314-316 in the bases 320-322 is for illustration only and that the actuators 314-316 could have any other suitable locations.

The actuator controller 318 controls the operation of the actuators 314-316 in order to control the spacing between the scanning head 304 and the web 302. For example, the scanning head 304 could include at least one distance sensor 324 configured to measure a distance to the web 302. The scanning head 304 could provide measurements from the distance sensor 324 to the actuator controller 318, such as via a wired or wireless connection. The actuator controller 318 can use the measurements to cause the actuators 314-316 to raise or lower the vertical supports 308-310 as the scanning head 304 moves along the support 312. Among other things, the actuator controller 318 could control the actuators 314-316 so that the scanning head 304 has a desired spatial relationship with the web 302.

The actuator controller 318 includes any suitable structure for controlling the operation of an actuator system to vary the raising and lowering of support structures in a scanner. For example, the actuator controller 318 could include one or more processing devices 326 configured to execute instructions or perform various tasks, such as one or more microprocessors, microcontrollers, digital signal processors, field programmable gate arrays, application specific integrated circuits, or discrete logic devices. The actuator controller 318 could also include one or more memories 328 configured to store instructions and data used, generated, or collected by the processing device(s) 142. The data could include measurements from the distance sensor(s) 324. The actuator controller 318 could further include at least one interface 330 configured to communicate with actuators, distance sensors, and other components, such as one or more Ethernet interfaces or wireless transceivers.

Each distance sensor 324 represents any suitable structure configured to measure distance. Example techniques that could be used to measure distance include optical triangulation techniques (such as laser triangulation), proximity sensing (such as with capacitive or ultrasound sensors), structured light and camera sensing, stereographic techniques, interferometric techniques, Moiré fringe and other interference techniques, laser speckle techniques, and contact techniques.

Note that the actuator controller 318 could control the actuators 314-316 in any suitable manner to help provide desired positioning of the scanning head 304 with respect to the web 302. For example, the actuator controller 318 could cause the actuators 314-316 to simultaneously raise or lower the vertical supports 308-310 in unison. If the overall frame is adequately flexible, the actuator controller 318 could also cause one actuator 314-316 to raise or lower its vertical support 308-310 while the other actuator 314-316 keeps its vertical support 308-310 stationary. Further, if the overall frame is adequately flexible, the actuator controller 318 could cause the actuators 314-316 to move the vertical supports 308-310 in opposite directions.

The actuator controller 318 could also use any suitable technique to determine how to adjust the actuators 314-316 in order to achieve a desired positioning of the scanning head 304 relative to the web 302. For example, the actuator controller 318 could receive distance measurements from the distance sensor(s) 324 and adjust the actuators 314-316 up or down until the distance measurements reach a desired value or are within a desired range of values. As another example, the actuator controller 318 could use one or more models stored in a memory 328 or elsewhere to control the actuators 314-316. For instance, a model could define how the actuators 314-316 should be controlled to create a specified amount of change in the distance between the scanning head 304 and the web 302. The actuator controller 318 could receive distance measurements from the distance sensor 324 and use the model to determine how to adjust the actuators 314-316. Note that any other suitable technique could be used by the actuator controller 318 to determine how to adjust the actuators 314-316.

In the example shown in FIG. 3A, the scanning head 304 is positioned above the web 302. However, the scanning head 304 could alternatively be positioned below the web 302, along with the connecting support 312. It is also possible to have multiple scanning heads on a single side of the web 302. For example, multiple scanning heads 304 could be mounted to the support 312 and used to capture measurements of overlapping or non-overlapping zones of the web 302, where suitable control is used to help ensure that the scanning heads 304 do not contact one another. One example approach for using multiple scanning heads on a common support is provided in U.S. patent application Ser. No. 14/497,057 (which is hereby incorporated by reference in its entirety).

It is further possible to have multiple scanning heads positioned on opposite sides of a web. An example of this is shown in FIG. 3B, which illustrates a system 350 that includes multiple scanning heads 304a-304b configured to measure one or more characteristics of the web 302. In this example, the frame includes multiple supports 312a-312b. The scanning head 304a is positioned above the web 302 and travels along the support 312a, while the scanning head 304b is positioned below the web 302 and travels along the support 312b. Again, while the supports 312a-312b are shown here as bending upward, each support 312a-312b could be substantially horizontal, bend downward, or have other any other regular or irregular path. Also, the supports 312a-312b need not have identical shapes.

At least one of the scanning heads 304a-304b includes at least one distance sensor 324a-324b. In some embodiments, only one scanning head 304a-304b may include a distance sensor(s), and the actuator controller 318 can use measurements from the distance sensor(s) to cause the actuators 314-316 to keep the associated scanning head at a desired position relative to the web 302. If the scanning head without a distance sensor is mounted at a known distance from the scanning head with a distance sensor (such as when the supports 312a-312b are mounted at a known distance apart), both scanning heads can be kept at desired positions relative to the web 302 when one scanning head is positioned properly.

In other embodiments, each of the scanning heads 304a-304b could include one or more distance sensors 324a-324b, and the actuator controller 318 can use measurements from both scanning heads to cause the actuators 314-316 to keep the web 302 at a desired position between the scanning heads. For example, the vertical supports 308-310 could be moved up or down to maintain the web 302 substantially centered between the scanning heads 304a-304b. Note, however, that any non-centered position could also be maintained.

While not shown, it is possible to have multiple scanning heads on one or both sides of the web 302. For example, multiple scanning heads 304a could be mounted to the support 312a, and/or multiple scanning heads 304b could be mounted to the support 312b. Scanning heads on a common side of the web 302 could be used to capture measurements of overlapping or non-overlapping zones of the web 302, and suitable control can be used to help ensure that the scanning heads on the common side do not contact one another.

Although FIGS. 3A and 3B illustrate examples of systems 300, 350 for adjusting a measurement position of a scanning head, various changes may be made to FIGS. 3A and 3B. For example, the shapes and overall structures of the frames shown in FIGS. 3A and 3B are for illustration only. Any other suitable support structure(s) could be used to support one or more scanning heads, as long as part or all of the support structure(s) can be moved to alter the spatial relationship between a web and one or more scanning heads.

Figure 4:
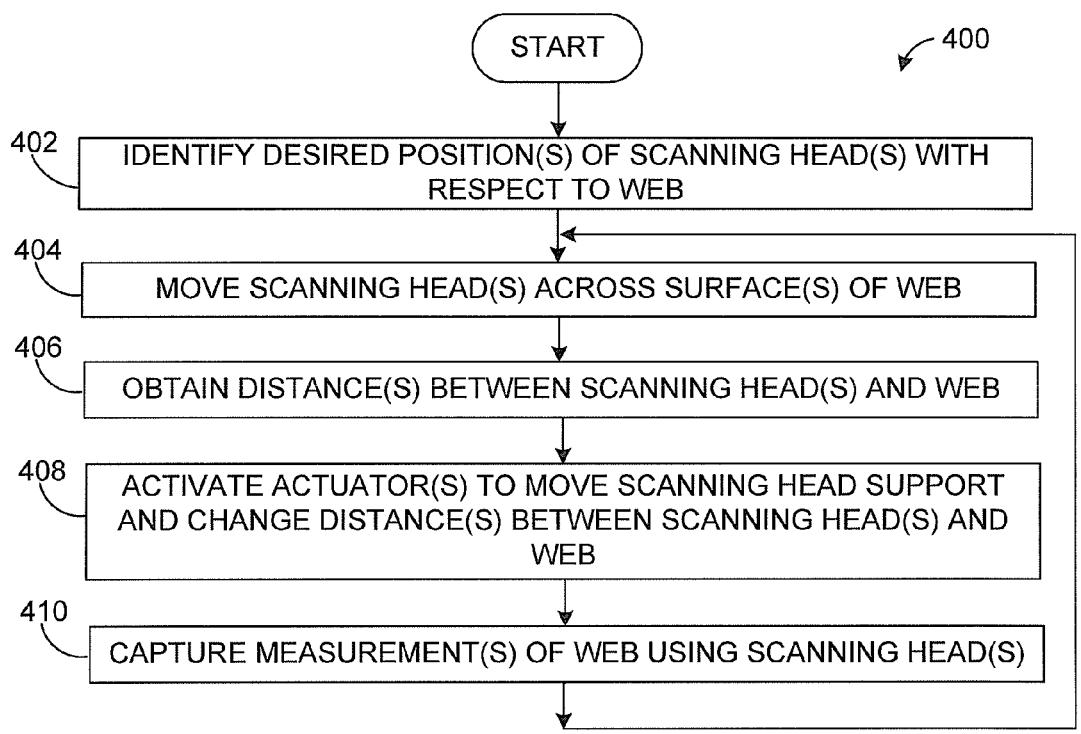
FIG. 4 illustrates an example method for adjusting a measurement position of a scanning head according to this disclosure.

FIG. 4 illustrates an example method 400 for adjusting a measurement position of a scanning head according to this disclosure. As shown in FIG. 4, at least one desired position of one or more scanning heads with respect to a web is identified at step 402. This could include, for example, the actuator controller 318 identifying a desired amount of offset between the web 302 and one or more scanning heads 304. This could also include the actuator controller 318 identifying a desired position of the web 302 between multiple scanning heads 304a-304b. The desired position could be identified in any suitable manner, such as by using input from a user or input from the controller 104 or other device. In some embodiments, the desired position can vary depending on the type(s) of sensor measurement(s) to be captured by the scanning head(s).

The one or more scanning heads are moved across one or more surfaces of the web at step 404. This could include, for example, using motors or other driving mechanisms to move the scanning head(s) 304, 304a-304b along the associated support(s) 312, 312a-312b. Each scanning head could be moved across part or all of the surface of the web 302.

One or more distances between the scanning head(s) and the web are obtained at step 406. This could include, for example, the interface 330 of the actuator controller 318 receiving distance measurements from the distance sensor(s) 324, 324a-324b of the scanning head(s) 304, 304a-304b. Note that the distance measurements here could represent any suitable values, such as measurements of absolute distance or measurements of relative distance from a target value.

One or more actuators are activated in order to move at least one scanning head support, which changes the one or more distances between the scanning head(s) and the web, at step 408. This could include, for example, the processing device 326 of the actuator controller 318 generating control signals for causing the actuators 314-316 to raise or lower the vertical supports 308-310 in order to change the distance(s) between the scanning head(s) 304, 304a-304b and the web 302. As noted above, the vertical supports 308-310 could be raised or lowered in unison, or one vertical support could be moved in one direction while the other vertical support is kept stationary or moved in the opposite direction.

One or more measurements of the web are captured using the scanning head(s) at step 410. This could include, for example, using one or more sensors 306 of the scanning head(s) 304, 304a-304b to capture any of a wide variety of measurements of the web 302.

The overall process shown in FIG. 4 could be repeated any number of times. Also, measurements of a web can be captured continuously or intermittently.

Although FIG. 4 illustrates one example of a method 400 for adjusting a measurement position of a scanning head, various changes may be made to FIG. 4. For example, while shown as a series of steps, various steps in FIG. 4 could overlap, occur in parallel, occur in a different order, or occur any number of times. As a particular example, steps 404-410 could completely or partially overlap so that distance measurements are captured and actuators are used as one or more scanning heads move across a web and capture measurements. As another particular example, step 402 could occur continuously or intermittently, such as whenever a change in sensor measurements requires a corresponding change in web position relative to the scanning head(s).

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "communicate" and "receive," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
   a frame configured to support at least one scanning head as the at least one scanning head moves back and forth across at least one surface of a web of material; and
   an actuator system configured to move at least a portion of the frame to alter a position of the at least one scanning head relative to the web.

2. The system of claim 1, wherein the actuator system comprises a controller configured to:
   receive distance measurements from the at least one scanning head, the distance measurements identifying measured distances to the web of material; and
   control one or more actuators that are configured to move at least the portion of the frame.

3. The system of claim 2, wherein the controller is configured to control the one or more actuators so that the at least one scanning head maintains a substantially fixed offset from the web as the at least one scanning head moves back and forth across the at least one surface of the web.

4. The system of claim 2, wherein:
   the frame is configured to support multiple scanning heads as the scanning heads move back and forth across multiple surfaces of the web; and
   the controller is configured to control the one or more actuators so that the web maintains a substantially fixed position between the scanning heads as the scanning heads move back and forth across the surfaces of the web.

5. The system of claim 1, wherein:
   the frame comprises multiple first supports and a second support connected to the first supports;
   the second support is configured to receive the at least one scanning head; and
   the actuator system is configured to move each of the first supports.

6. The system of claim 5, wherein the frame further comprises a third support connected to the first supports, the third support configured to receive at least one additional scanning head.

7. The system of claim 6, wherein:
   the second and third supports are separated at a known distance; and
   the controller is configured to use the known distance to control the one or more actuators so that the web maintains a substantially centered position between the scanning heads.

8. The system of claim 1, wherein the actuator system comprises multiple linear actuators.

9. An apparatus comprising:
   at least one interface configured to receive distance measurements from at least one scanning head that moves back and forth across at least one surface of a web of material on a frame, the distance measurements identifying measured distances to the web of material; and at least one processing device configured to control one or more actuators in order to move at least a portion of the frame to alter a position of the at least one scanning head relative to the web.

10. The apparatus of claim 9, wherein the at least one processing device is configured to control the one or more actuators so that the at least one scanning head maintains a substantially fixed offset from the web as the at least one scanning head moves back and forth across the at least one surface of the web.

11. The apparatus of claim 9, wherein:
the at least one interface is configured to receive distance measurements from multiple scanning heads that move back and forth across multiple surfaces of the web; and
the at least one processing device is configured to control the one or more actuators so that the web maintains a substantially fixed position between the scanning heads as the scanning heads move back and forth across the surfaces of the web.

12. The apparatus of claim 11, wherein the at least one processing device is configured to control the one or more actuators so that the web remains substantially centered between the scanning heads as the scanning heads move back and forth across the surfaces of the web.

13. The apparatus of claim 12, wherein the controller is configured to use a known distance between multiple supports of the frame along which the scanning heads move to control the one or more actuators.

14. The apparatus of claim 9, further comprising:
a memory configured to store one or more models, the at least one processing device configured to control the one or more actuators using the one or more models.

15. A method comprising:
receiving distance measurements from at least one scanning head that moves back and forth across at least one surface of a web of material on a frame, the distance measurements identifying measured distances to the web of material; and
controlling one or more actuators in order to move at least a portion of the frame to alter a position of the at least one scanning head relative to the web.

16. The method of claim 15, wherein the one or more actuators are controlled so that the at least one scanning head maintains a substantially fixed offset from the web as the at least one scanning head moves back and forth across the at least one surface of the web.

17. The method of claim 15, wherein:
the distance measurements are received from multiple scanning heads that move back and forth across multiple surfaces of the web; and
the one or more actuators are controlled so that the web maintains a substantially fixed position between the scanning heads as the scanning heads move back and forth across the surfaces of the web.

18. The method of claim 17, wherein the one or more actuators are controlled so that the web remains substantially centered between the scanning heads as the scanning heads move back and forth across the surfaces of the web.

19. The method of claim 17, wherein a known distance between multiple supports of the frame along which the scanning heads move is used to control the one or more actuators.

20. The method of claim 15, wherein controlling the one or more actuators comprises generating control signals for one or more linear actuators, the linear actuators configured to raise and lower multiple supports of the frame.

* * * * *